United States Patent [19]

Rivers et al.

[11] Patent Number: 5,347,004
[45] Date of Patent: Sep. 13, 1994

[54] MIXTURES OF HEXAHYDROTRIAZINES USEFUL AS H2S SCAVENGERS

[75] Inventors: Gordon T. Rivers, Houston; Richard L. Rybacki, Katy, both of Tex.

[73] Assignee: Baker Hughes, Inc., Houston, Tex.

[21] Appl. No.: 959,223

[22] Filed: Oct. 9, 1992

[51] Int. Cl.$^5$ .................................. C07D 251/04
[52] U.S. Cl. ..................... 544/180; 544/216
[58] Field of Search ........................ 544/180, 216

[56] References Cited

U.S. PATENT DOCUMENTS

| | | | |
|---|---|---|---|
| 2,729,679 | 1/1956 | Anderson | 544/180 |
| 4,266,054 | 5/1981 | Au | 544/215 |
| 4,523,947 | 6/1985 | Szczepanski et al. | 544/180 |
| 4,894,178 | 1/1990 | Ho et al. | 252/189 |

FOREIGN PATENT DOCUMENTS 0438812 7/1991 European Pat. Off. .
9201481 2/1992 PCT Int'l Appl. .

*Primary Examiner*—Mukund J. Shah
*Assistant Examiner*—Y. N. Gupta
*Attorney, Agent, or Firm*—Rosenblatt & Associates

[57] ABSTRACT

A mixture of amines made by reacting an amine compound with an aldehyde compound has been found to reduce the levels of H2S in liquid or gaseous hydrocarbon streams. At least one of the compounds must have an alkoxyalkylene radical. In one embodiment of the invention, the mixture of amines contains at least one hexahydrotriazine compound of the formula:

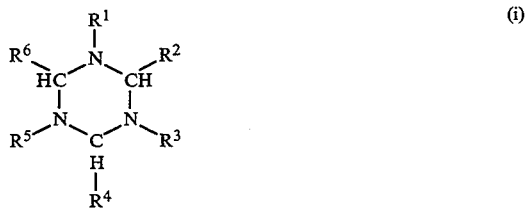

where $R^1$, $R^2$, $R^3$, $R^4$, $R^5$ and $R^6$ are independently selected from the group consisting of hydrogen and an alkyl radical, including substituted alkyl radicals, of 1 to 5 carbon atoms; where at least one of the groups is an alkoxyalkylene group. In another embodiment of the invention, the amine mixture may contain other by products, such as the monomers which make up the hexahydrotriazine, with or without the hexahydrotriazine being present. These materials are selective to the reduction of H2S levels in hydrocarbon or aqueous streams in the presence of CO2 which does not compromise their performance.

24 Claims, 3 Drawing Sheets

MIXTURES OF HEXAHYDROTRIAZINES USEFUL AS H₂S SCAVENGERS

FIELD OF THE INVENTION

The invention relates to chemical compositions for reaction with hydrogen sulfide ($H_2S$), and, in one aspect, more particularly relates to hexahydrotriazines alone or together with amine coproducts useful in reducing the level of $H_2S$ in hydrocarbon streams.

BACKGROUND OF THE INVENTION

The removal of $H_2S$ from a liquid or gaseous hydrocarbon stream is a problem that has long challenged workers in many industries. For example, one such area is the petroleum industry where the $H_2S$ content of certain crudes recovered from oil field reservoirs in many areas of the world is too high for commercial acceptance. The same is true for recovered natural gas streams. The presence of $H_2S$ presents many environmental and safety hazards in that it is highly flammable, is toxic by inhalation, and is a strong irritant to eyes and mucous membranes. In addition, the presence of such sulfur-containing compounds may result in the deposition of sulfur-containing salts which can cause plugging and corrosion of transmission pipes, valves, regulators and the like. Even if the natural gas is flared as a waste stream from petroleum production, it is necessary that the $H_2S$ either be completely removed or at least reduced to a level where the combustion products from the flaring do not introduce deleterious amounts of pollutants such as, for example sulfur dioxide, $SO_2$, a component of "acid rain."

Since $H_2S$ has an offensive odor and natural gas containing it is often called "sour" gas, treatments to reduce or remove $H_2S$ are often termed "sweetening". When a particular compound or agent is used to remove or reduce $H_2S$ levels, the agent is sometimes referred to as a scavenging agent. The sweetening or removal of $H_2S$ from petroleum or natural gas is only one example of where $H_2S$ level reduction or removal must be performed. In the manufactured gas industry or the coke-making industry, coal gas containing unacceptable amounts of $H_2S$ is commonly produced by the destructive distillation of bituminous coal having high sulfur content. Another $H_2S$ contamination problem is found in the manufacture of water gas or synthesis gas where it is not unusual to produce gas streams containing $H_2S$ by passing steam over a bed of incandescent coke or coal containing a minor amount of sulfur. $H_2S$ removal is also a frequently encountered problem in the petroleum industry because the principal raw material, crude oil, typically contains minor amounts of sulfur—principally in the form of organic sulfur compounds. During the course of the many processes to which the crude oil or fractions thereof are subjected, one or more gas streams containing $H_2S$ often result.

Regardless of the source of the liquid or gas stream, the problem of removing or reducing $H_2S$ levels therefrom has been solved in numerous different ways in the past which generally involve one or more of the following techniques: selective absorption with a wide variety of absorbents; absorption by suitable absorbent; and selective reaction with a reagent which produces a readily separable product. The details of these techniques are known to those skilled in the art. Indeed, a number of systems using amines, aldehydes, alcohols, and reaction products of these materials are known. The voluminous number of prior art processes, patents and publications concerning the removal of $H_2S$ from liquid and gas streams testifies to the facts that (a) the desirability and necessity of removing the $H_2S$ from the streams, and (b) that up to now no completely desirable process has been found. There remains a continuing need for improved processes and compounds to reduce and/or remove the presence of $H_2S$ in liquid and gaseous hydrocarbon streams.

SUMMARY OF THE INVENTION

Accordingly, it is an object of the present invention to provide new compositions of matter effective in the reduction of $H_2S$ in liquid and gaseous hydrocarbon streams.

It is another object of the present invention to provide a method for producing new compositions of matter for reducing $H_2S$ levels, which method may be readily and easily performed.

It is yet another object of the invention to provide a mixture of effective compositions of matter for reducing $H_2S$ levels, which mixture may be used "as is" without separation.

In carrying out these and other objects of the invention, there is provided, in one form, a hexahydrotriazine of the formula:

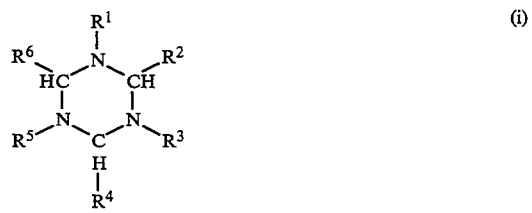

(i)

where $R^1$, $R^3$ and $R^5$ are independently selected from the group consisting of hydrogen and a straight or branched alkyl radical, including substituted alkyl radicals, of 1 to 5 carbon atoms; where $R^2$, $R^4$ and $R^6$ are independently selected from the group consisting of hydrogen and a straight or branched alkyl radical, including substituted alkyl radicals, of 1 to 5 carbon atoms; and where at least one of the R groups is an alkoxyalkylene group.

DETAILED DESCRIPTION OF THE INVENTION

Figure 1:
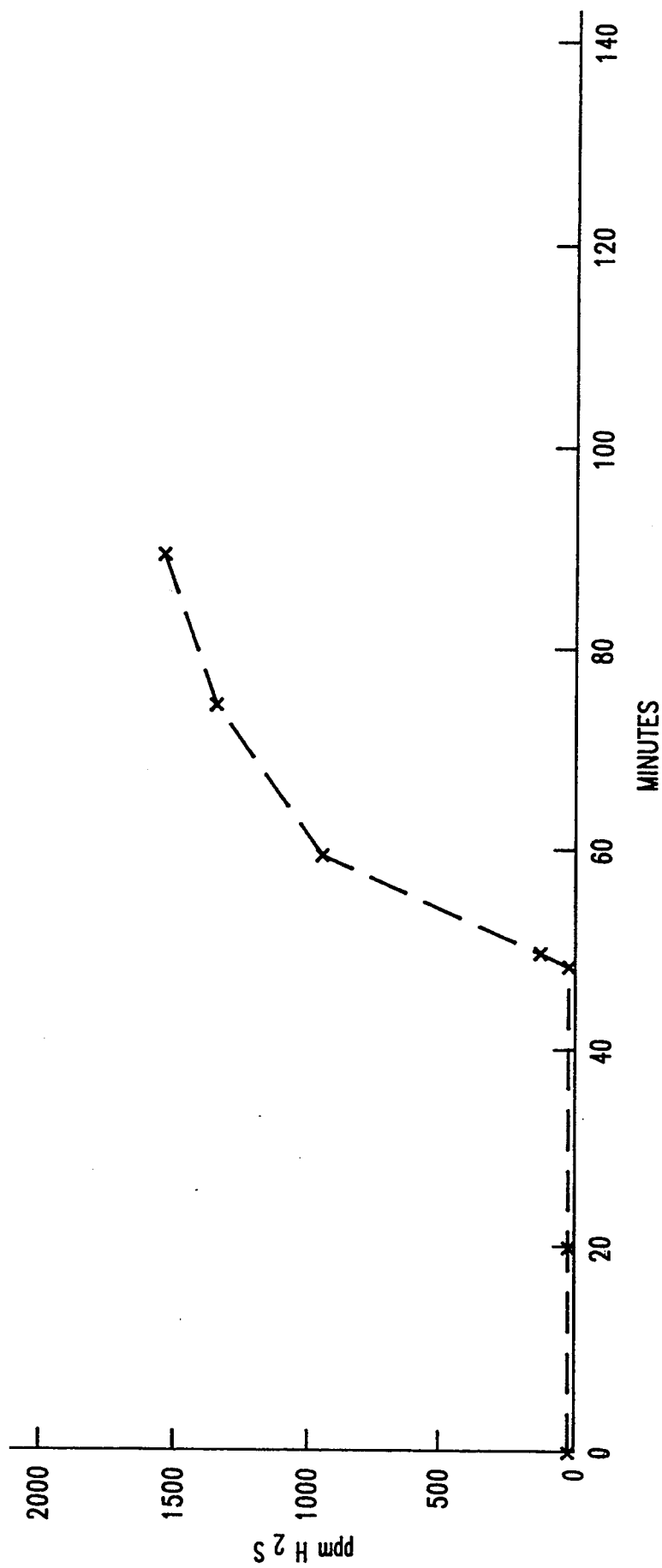
FIG. 1 is a graph of $H_2S$ level over time using Gas Tech ® stain tubes for the Example 1 material applied to a test gas mixture of 2000 ppm $H_2S$, 1% $CO_2$, the balance being methane, at a rate of 5.5 SCFH and 20 psig as described in Example 2.
Figure 2:
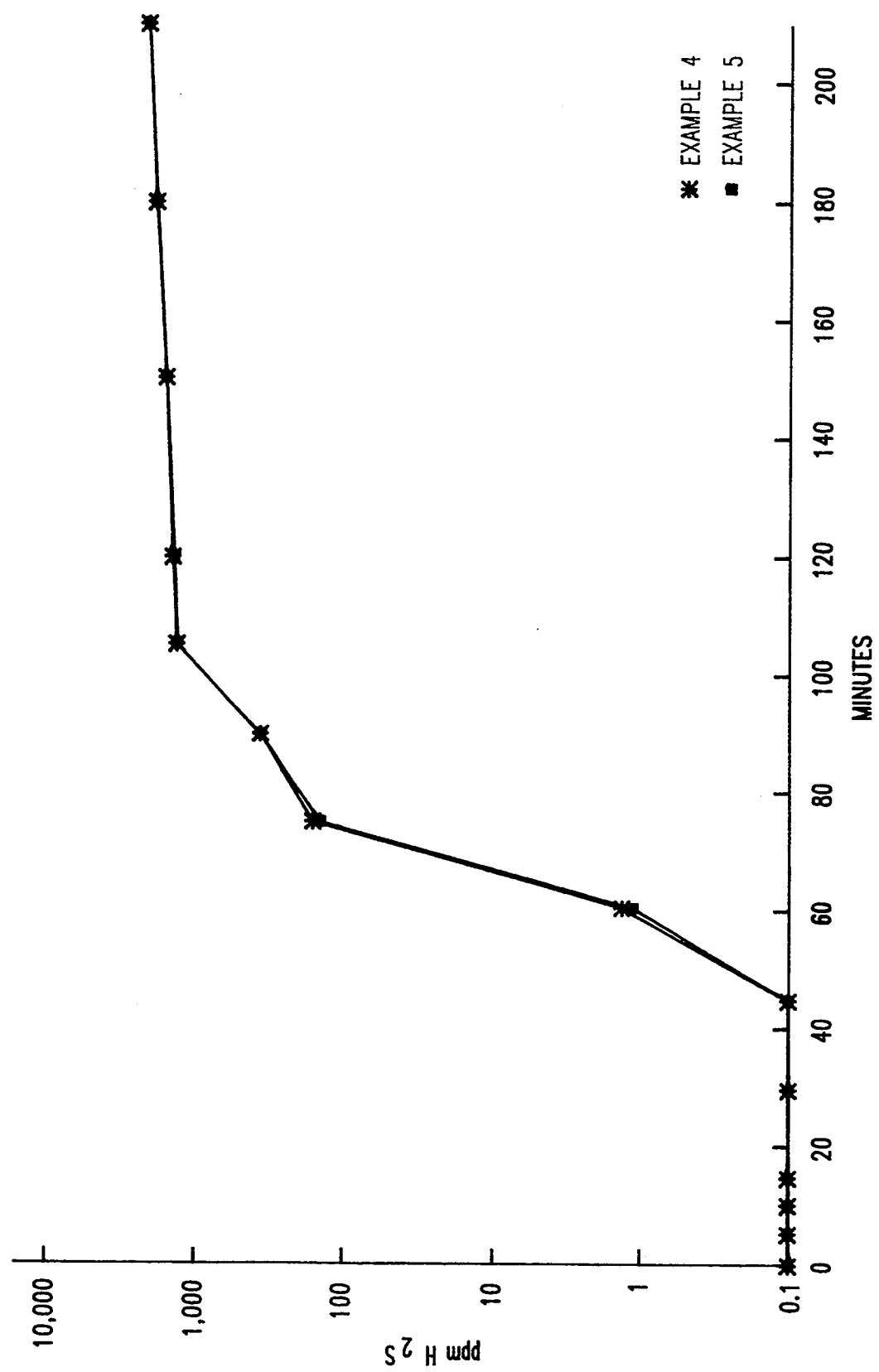
FIG. 2 is a graph of $H_2S$ level over time similar to that of FIG. 1 except that the ordinate $H_2S$ ppm level is logarithmic and the materials used are those from Examples 4 and 5.

It has been discovered that primary amines, mixtures of primary amines or mixtures of primary and secondary amines may be reacted with aldehydes such as formaldehyde to form hexahydrotriazines, mixtures of hexahydrotriazines, diaminoalkanes and/or dialkylaminoalkanols. These compounds are useful as $H_2S$ scavengers or sweetening agents. The reaction products or blends of alkoxyalkylene amines, ammonia, and dialkylamines with aldehydes may be described in general by the schematic reaction as follows:

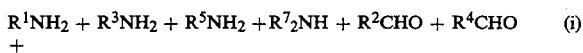
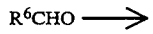

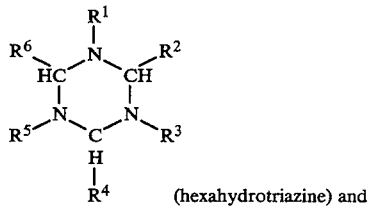 (hexahydrotriazine) and

where $R^1$, $R^3$ and $R^5$ are independently selected from the group consisting of hydrogen and a straight or branched alkyl radical, including substituted alkyl radicals, of 1 to 5 carbon atoms; and where $R^2$, $R^4$ and $R^6$ are independently selected from the group consisting of hydrogen and a straight or branched alkyl radical of 1 to 5 carbon atoms; where R may independently be $R^1$, $R^2$, R3, $R^4$, R5 and R6, and where R' may independently be alkylene radicals equivalent to $R^1$, $R^2$, $R^3$, $R^4$, $R^5$ and $R^6$. At least one of the groups $R^1$, $R^2$, $R^3$, $R^4$, $R^5$ and $R^6$ is an alkoxyalkylene group. The term $R^7$ is independently $R^1$, $R^3$ or $R^5$. R may independently be $R^1$, $R^2$, $R^3$, $R^4$, $R^5$ and $R^6$, while R' may independently be alkylene radicals corresponding to or equivalent to $R^1$, $R^2$, $R^3$, $R^4$, $R^5$ and $R^6$. That is, R' would be the $R^1$, $R^2$, $R^3$, $R^4$, R5 and R6 structures having one less hydrogen. The valence previously satisfied by the hydrogen would be bonded as shown in structures (iii) and (iv).

It will be appreciated that the distribution of the amine products between structures (i), (ii), (iii) and (iv) will vary depending on a variety of factors. For example, an amine:aldehyde reactant mole ratio of close to 1:1 will tend to favor products of structures (i), (ii) and (iv). An amine:aldehyde reactant mole ratio of close to 2:1 will tend to favor products of structures (iii). Use of lower amines (e.g. methylamine) or lower aldehydes (e.g. formaldehyde) will tend to favor the heterocyclic polymeric structures (i) over monomer structures such as (ii), whereas employing higher amines or aldehydes will tend to favor the monomer structures (ii) rather than the polymer structures (i). All structures are believed to be effective in $H_2S$ scavenging. In one embodiment of the invention, the trimer triazine products (i) are most preferred; the structures (ii) and (iv) are next preferred, and the dimer products (iii) are the relatively least preferred In one embodiment of the invention, the invention concerns the new hexahydrotriazine compositions of matter (i) and the mixture of amines should have at least one compound of the structure (i). In another embodiment of the invention, the mixture of amines must have at least one amine from the total group consisting of (i) hexahydrotriazine, (ii), (iii) or (iv). In one embodiment, at least one species in the mixture of amines, (i), (ii), (iii) and/or (iv), must have an alkoxyalkylene group on a nitrogen or substituted methylene group between two nitrogens, where the alkoxyalkylene group has the structure $R^8$—O—$R^9$ where $R^8$ are independently alkyl radicals and $R^9$ are independently alkylene radicals, each of 1 to 5 carbon atoms.

Amine compounds or reactants which have been proven under the preparations and uses of this invention include, but are not necessarily limited to, 3-methoxypropylamine ($CH_3OCH_2CH_2CH_2NH_2$; sometimes noted as MOPA); 3-ethoxypropylamine; ammonia ($NH_3$); methylamine ($CH_3NH_2$); dimethylamine ($CH_3NHCH_3$); 1-methoxyisopropylamine [$CH_3OCH_2CH(NH_2)CH_3$, also known by the product name of Jeffamine® M-89 amine sold by Texaco Chemical Co.] and mixtures thereof.

The aldehydes proved to be useful in this invention include, but are not necessarily limited to formaldehyde (including its various forms, e.g. paraformaldehyde, formalin, etc.), acetaldehyde, etc.

Other amines and monoaldehydes expected to be useful include, but are not necessarily limited to, hydroxylamine ($HONH_2$); $C_mH_nOC_pH_qNH_2$; $C_pH_rNH_2$; $C_mH_nCHO$; $(C_mH_n)(C_pH_r)NH$; $XC_mH_qNH_2$; $XNH_2$; where m = 1 to 5;
n = 3 to 11;
p = 2 to 5;
q = 2 to 10;
r = 5 to 11;
X includes, but is not limited to $SO_3H$, $CO_2H$, or their salts.

The amine reactants to aldehyde reactants molar ratio may range from about 10:1 to 1:10. It is preferred that the amine to aldehyde molar ratio be in the range from about 1.2:1 to 1:1.2. The molar ratio of alkoxyalkyleneamine to all other amines used as reactants may range from about 1:0 to 1:100, preferably from about 1:0 to 1:9.

It has been further discovered that the addition of a dialdehyde at some point in the process has a beneficial effect. For example, in one embodiment, the amine compound and the aldehyde compound are reacted together in a first step and then the dialdehyde is added in a second step. At this point in the development of the invention, it is unclear whether the dialdehyde is reacting to give an unknown product or if the dialdehyde is simply blended with the reaction products of the amine compound and the aldehyde compound. In any event, it is observed that the addition of the dialdehyde gives products with better results for scavenging $H_2S$ than when it is absent. Alternatively, the dialdehyde may be added with the monoaldehyde compound in the first step for reaction with the amine compound. In yet another embodiment, in the two-step process, there may be added between the first and second steps the reaction product of a second amine compound and a second aldehyde compound. Generally, the second amine compound is different from the first amine compound or the second aldehyde compound is different from the second aldehyde compound, or both. There is no advantage for the second amine compound and second aldehyde compound to be the same as in the first step.

Suitable dialdehydes for the enhanced embodiment of the invention include, but are not necessarily limited to, glyoxal; glutaraldehyde; succinic aldehyde; 1,6-hexane dialdehyde (adipic aldehyde) and mixtures thereof. Glyoxal is particularly preferred.

It is additionally anticipated that a dialdehyde, such as those described above, may be advantageously blended and/or reacted with known triazine $H_2S$ scavengers to give improved results. For example, the reaction of alkanolamines having 1 to about 6 carbon atoms (e.g. monoethanolamine, MEA) with lower aldehydes having I to about 4 carbon atoms (e.g. formaldehyde) give triazines having $H_2S$ scavenging ability. Specifically, the reaction of MEA with $CH_2O$ gives

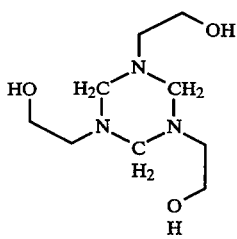

1, 3, 5-tris-(2-hydroxyethyl)-hexahydro-D-triazine

More details about such known triazines are given in U.S. Pat. No. 4,978,512, incorporated by reference herein.

Although the subject is still being developed, it is anticipated that the amines and mixtures of amines of this invention may be employed without the need of alcohols (mono-ols, e.g. methanol) or diols (e.g. ethylene glycol) as antifreeze or polymerization inhibitor additives, particularly in concentrated form. However, it is also anticipated that under some conditions, such as high dilution of the amine mixture, that the addition of an antifreeze agent such as an alcohol or diol might be desired.

In one embodiment of the invention, the amine compound and the aldehyde compound are reacted at a temperature in the range of about 0° to 150° C. Reaction temperatures hotter than 150° C. would probably encourage other condensation reactions to the detriment of the desired reaction herein. A preferred temperature range is from about 20° to 75° C. In many cases, the reaction of the amine compound with the aldehyde compound may be exothermic without the necessity of adding heat, and, of course, this would be preferred. The pressure range for the reaction of this invention is from atmospheric to about 200 psig, more preferably from about atmospheric to about 30 psigh. The reaction may be carried out in aqueous solution, which is preferred in most embodiments of the invention. The amine mixtures of this invention are liquids and react essentially instantaneously with any $H_2S$ in the hydrocarbon stream. The presence of $CO_2$ in the hydrocarbon stream does not compromise the scavenging of $H_2S$ by the amine(s) of the invention. Curiously, it has been observed that when both $H_2S$ and $CO_2$ are present in the stream, the amine scavenger(s) will absorb (react with) both $H_2S$ and $CO_2$ and the levels of both will drop. However, after a time, the $CO_2$ level will no longer drop but the $H_2S$ content will continue to decrease. Without being limited to any particular explanation, it may be that the amine(s) will initially react with whichever of $H_2S$ or $CO_2$ is contacted first, but that the amine(s) would preferentially bind with $H_2S$ and will give up $CO_2$ when $H_2S$ is encountered, thus resulting in an overall selective scavenging of $H_2S$. However, additional work is required to confirm this mechanism. The $H_2S$-amine reaction products are liquids, not troublesome solids which would foul equipment.

It is difficult to predict with precision the dosage of the amine mixture of this invention required to lower or eliminate $H_2S$ in a hydrocarbon stream. An optimum application level will depend on a number of factors, including, but not limited to, the nature of the hydrocarbons in the stream, the level of $H_2S$, the particular nature of the amine mixture, etc. For example, it has been discovered that where both methylamine and MOPA are used together to make the amine mixture, that the effectiveness of the mixture increases with increasing MOPA proportion relative to methylamine. This also helps to explain the preference for an alkoxyalkylene group on the active amines. However, since MOPA is presently relatively more expensive than methylamine, economic considerations may prefer relatively more methylamine as the amine component.

Nevertheless within the wide range of factors to be considered, the molar ratio of active amine(s) to $H_2S$ may range from about 1:1.5 (0.67:1) to about 1:6 (0.17:1). Considerably less than a 1:1 molar ratio of amine scavenger to $H_2S$ need be used, especially if the amine mixture is heavy in triazine materials.

It will be further appreciated that the method of this invention is not limited to reducing or removing $H_2S$ in hydrocarbon streams, but may also be employed in streams partially or completely composed of aqueous or water-soluble materials.

The mixture of amines of this invention may be used in conventional "in-line" injection systems and injected at any point in-line suitable to allow the mixture to react with the gaseous or liquid stream, e.g. at the well-head, separators, etc. The amine mixture may also be used in conventional scrubber tower systems. Other applications of the amine mixtures of this invention in other conventional systems or systems to be developed will become apparent to those skilled in the art.

The invention will be described further in the following illustrative Examples, which are non-limiting and serve only to further teach the invention.

EXAMPLE 1

A solution of 26.42 g of 3-methoxypropylamine (MOPA) and 23.02 g of a 40 wt. % solution of methyl amine in water was stirred and cooled in an ice bath. A solution of 50.56 g of a 37 wt.% solution of formaldehyde in water was added dropwise at such a rate as to maintain the temperature of the reaction mixture below 60° C. The solution was stirred an additional 30 minutes after the addition was complete. This material was used in Example 2.

The reaction of Example 1 may be at least partially schematically illustrated by the diagram below. It will be appreciated that the reaction product is best characterized as a mixture of amines and that while some of the reaction products are known, all may not necessarily be accounted for in the Example 1 product. What are shown below are most possible reaction products.

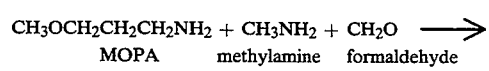

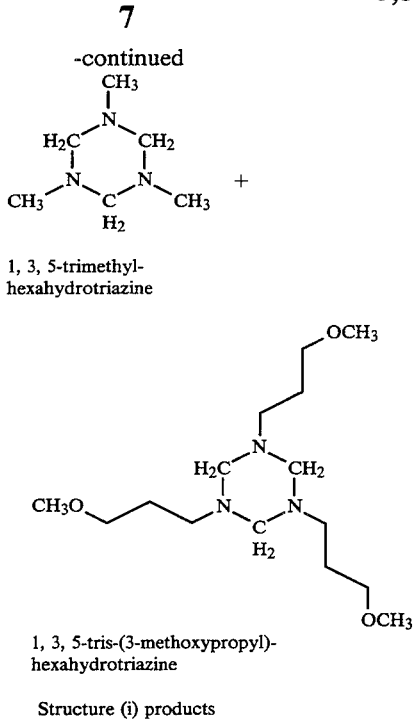

1, 3, 5-trimethyl-
hexahydrotriazine 1, 3, 5-tris-(3-methoxypropyl)-
hexahydrotriazine Structure (i) products Triazines would also be formed having mixed methyl ($CH_3$—) and methoxypropyl ($CH_3OCH_2CH_2CH_2$—) groups.

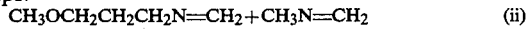

(ii)

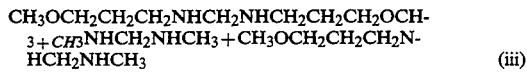

(iii)

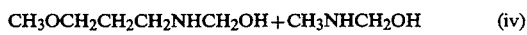

(iv)

As noted above, since a lower aldehyde, formaldehyde, was used, the structure (i) products are the more likely.

EXAMPLE 2

Ten grams of the reaction product of Example 2 was diluted to 100 g with deionized water. This sample was placed in a 1.25 in. column and sparged with a test gas mixture at a rate of 5.5 SCFFI and 20 psig. The composition of the test gas was 2000 ppm $H_2S$, 1% $CO_2$ and the balance methane. $H_2S$ readings were taken by Gas Tech ® stain tubes. Test data are shown in the FIG. 1 graph. As can be seen, essentially complete removal (99.995%) of $H_2S$ occurred during the first 50 minutes of the continuous test. After that, the treating amine was exhausted and the $H_2S$ level rose. These materials are unusual in that their elimination of $H_2S$ is so complete or "flat" over time and the exhaustion point occurs suddenly, instead of the $H_2S$ increasing gradually once used.

EXAMPLE 3

The following proportions have been discovered to be one preferred embodiment of the invention:

| Component | Wt. % |
| --- | --- |
| Methylamine | 40–50 |
| Paraformaldehyde | 20–24 |
| Methoxypropylamine | 5–20 |
| Glyoxal | 0–20 |

In one non-limiting process embodiment, methylamine is reacted with a portion of the paraformaldehyde in a first step. In a second step, MOPA is reacted with paraformaldehyde and then added to the mixture of amines from the first step in a third step to form an intermediate mixture. Then, in a fourth step, the glyoxal proportion is added to the intermediate mixture to form the final product mixture. As noted previously, the glyoxal may react with any amine present to form yet further amine products, but the invention should not be limited in this way.

A product mixture of amines with the above proportions was prepared in the laboratory and found effective to lower the level of $H_2S$ in a test fluid. This product has now been qualified for field-scale tests.

EXAMPLES 4–5

Examples 4 and 5 represent mixtures of amines made in accordance with this invention; both were separately made according to the following procedure:

In an 8 oz. pressure bottle were placed 80 grams of a 40% by weight solution of aqueous methylamine. A 10 gram portion of paraformaldehyde was added. The bottle was mechanically shaken for about 40 minutes. The paraformaldehyde exothermically depolymerized and reacted with the amine to give a clear, colorless solution. A maximum temperature of about 70° C. was obtained. The solution was cooled to about ambient temperature. Then, three sequential 10 gram portions of paraformaldehyde were added and reacted as described for the first portion. A slight amount of suspended solid paraformaldehyde remained after the fourth addition and reaction. The mixture was cooled to ambient temperature and a 40 gram portion of 3-methoxypropylamine (MOPA) was added. The solution was mechanically shaken for about 40 minutes and then cooled to ambient temperature. A 40 gram portion of a 40% by weight solution of aqueous glyoxal was added dropwise with intermittent mixing by shaking to give a clear yellow solution.

The amine mixture products from Examples 4 and 5 were tested using a continuous flow of 5.5 SCFH, 20 psig methane containing 2000 ppm $H_2S$ and 1% $CO_2$. Using 5% active solutions in a bubble tower test, both amine mixtures gave essentially identical results of essentially complete $H_2S$ removal until they were spent about 45 minutes into the test. Notice that the ppm $H_2S$ ordinate is logarithmic.

As in Example 2, the contaminated stream injected into the test apparatus had 2000 ppm as 100% of the $H_2S$ level. Here, there was 0.1 or less ppm $H_2S$ measured coming out for both materials. By calculation: 0.1/2000=0.00005 or 0.005% $H_2S$ was present in the stream exiting. Stated another way, 99.9995% $H_2S$ reduction was achieved.

EXAMPLE 6

Figure 3:
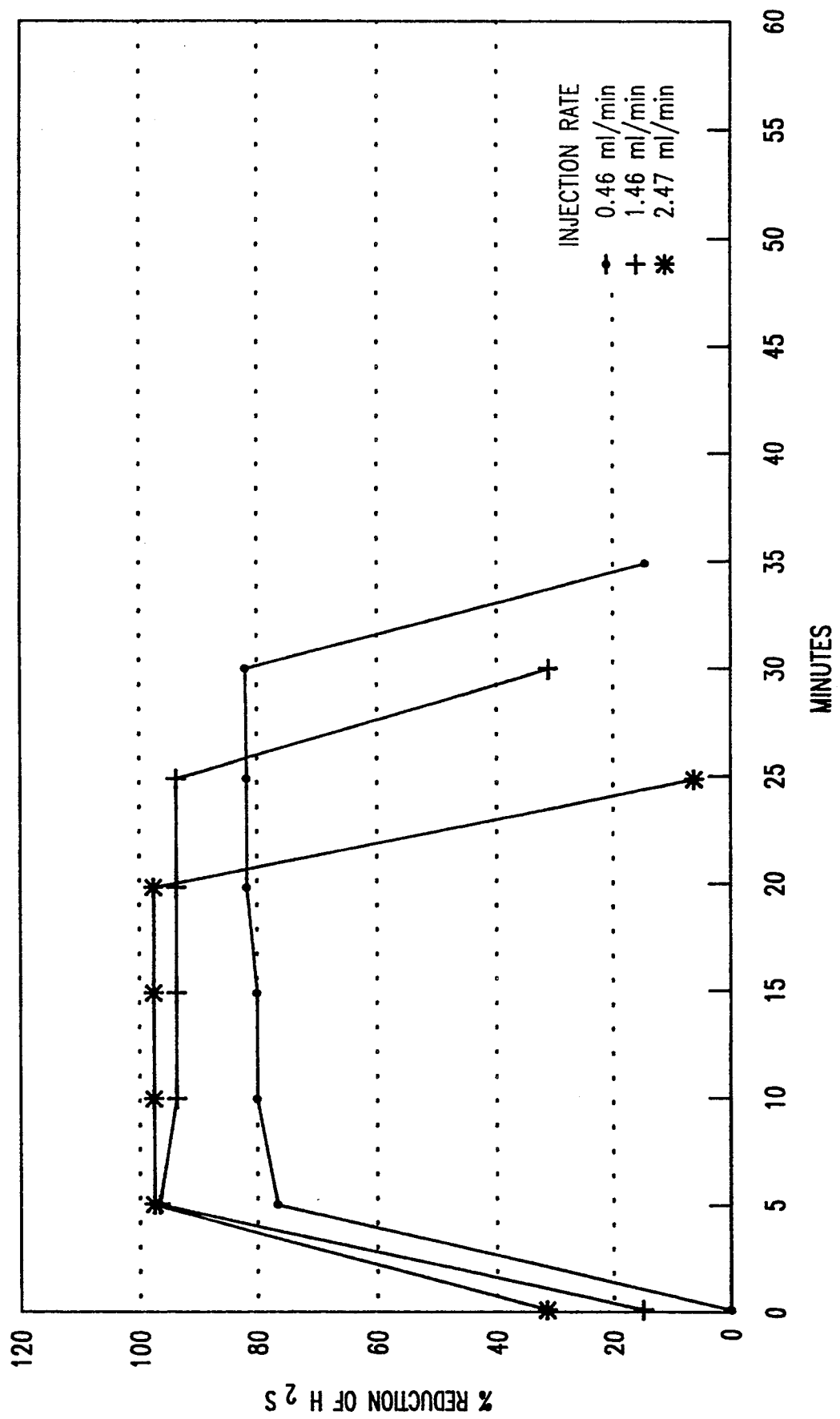
FIG. 3 is a graph of $H_2S$ level over time, where the $H_2S$ level along the ordinate is expressed in terms of % reduction of $H_2S$ in a methane stream of 27 SCFM, 264 psig, having 35 ppm $H_2S$ and 0.75% $CO_2$ at 112° F. Various injection rates of the Example 4 material were tested.

Example 6 involves using the material from Example 4 at various flow rates to reduce the level of $H_2S$ in a methane stream of 27 SCFM, 264 psig, having 35 ppm $H_2S$ and 0.75% $CO_2$ at 112° F. The results are given in FIG. 3. The strongly sloped portions at the beginnings and ends of the curves may be essentially ignored as these represent the time consumed in turning the pump on or off, and thus the system is rising or falling from steady state, respectively. It will be seen that an injection rate of 0.46 ml/min gave a reduction of about 80% in $H_2S$ level. The 1.45 ml/min injection rated reduced $H_2S$ by more than 95%, and the 2.47 ml/min injection rate gave essentially complete $H_2S$ removal.

EXAMPLE 7

2-Methoxyisopropylamine/$CH_2O$:1/1

In a 250 ml round bottom flask were placed 74.78 grams of 2-methoxyisopropylamine (Texaco Chemical Jeffamine M-89) and 31.4 grams of water. The stirred solution was cooled in a water bath and 108.86 grams of a 37% by weight solution of formaldehyde in water was added dropwise at such a rate as to keep the temperature below about 65° C. to give a clear, colorless solution. The resulting mixture of amines was shown to have the property of reducing $H_2S$ levels.

EXAMPLE 8

2-Methoxyethylamine/Methylamine/$CH_2O$: 1/1/2

In a 250 ml round bottom flask were placed 47.68 grams of 2-methoxyethylamine and 49.26 grams of a 40% by weight solution of aqueous methylamine. The stirred solution was cooled in a water bath and 103.06 grams of a 37% by weight solution of formaldehyde in water was added dropwise at such a rate as to keep the temperature below about 65° C. to give a clear, colorless solution. The resulting mixture of amines was shown to reduce $H_2S$ levels.

EXAMPLE 9

MOPA/Dimethylamine/$CH_2O$: 1/1/2

In a 250 ml round bottom flask were placed 50.68 grams of 3-methoxypropylamine and 61.00 grams of a 40% by weight solution of aqueous dimethylamine. The stirred solution was cooled in a water bath and 87.92 grams of a 37% by weight solution of formaldehyde in water was added dropwise at such a rate as to keep the temperature below about 65° C. to give a clear, colorless solution. Again, the resulting mixture of amines was shown to reduce $H_2S$ levels.

The mixtures of amines of this invention may result in the economic removal of $H_2S$ in cold weather and/or in the presence of $CO_2$. The mixture of amines, being selective to $H_2S$, will not be unnecessarily spent removing any $CO_2$ present. Indeed, relatively large amounts of $CO_2$ are not expected to adversely affect the $H_2S$ reduction method of this invention. The method of this invention is also applicable over a wide range of liquid or gaseous stream flow rates. While not being limited to any particular mechanism, it is anticipated that the amines of this invention react with $H_2S$ by molecular rearrangement and bonding, rather than by loose association, and thereby form stable products.

Many modifications may be made in the present invention without departing from the spirit and scope thereof which are defined only by the appended claims. For example, certain reaction products and mixtures thereof using alkoxyalkyleneamines and aldehydes other than those specifically set out herein may be found by one of routine skill in the art to be particularly advantageous. Further, the use of particular dialdehydes not explicitly mentioned as blending components or reactants may be later developed.

What is claimed is:

1. A hexahydrotriazine of the formula:

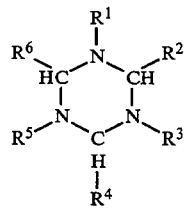

where $R^1$, $R^3$ and $R^5$ are independently selected from the group consisting of hydrogen and an alkyl radical, including substituted alkyl radicals, of 1 to 5 carbon atoms; and where $R^2$, $R^4$ and $R^6$ are independently selected from the group consisting of hydrogen and an alkyl radical, including substituted alkyl radicals, of 1 to 5 carbon atoms where at least one of the R groups, $R^1$, $R^2$, $R^3$, $R^4$, $R^5$ and $R^6$, is an alkoxyalkylene group.

2. A mixture of amine components comprising at least two of the following amines:

(i) a hexahydrotriazine of the formula:

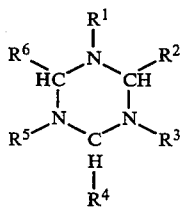

where $R^1$, $R^3$ and $R^5$ are independently selected from the group consisting of hydrogen and an alkyl radical, including substituted alkyl radicals, of 1 to 5 carbon atoms;

where $R^2$, $R^4$ and R6 are independently selected from the group consisting of hydrogen and an alkyl radical, including substituted alkyl radicals, of 1 to 5 carbon atoms; and (ii) RN=CHR;

(iii) $R_2NCH(R')NR_2$; and (iv) $R_2NCH(R')OH$;

where R may independently be $R^1$, $R^2$, $R^3$, $R^4$, RS and R6, and where R' may independently be alkylene radicals equivalent to $R^1$, $R^2$, $R^3$, $R^4$, $R^5$ and $R^6$; and where at least one of the groups $R^1$, $R^2$, $R^3$, $R^4$, $R^5$ and R6 is an alkoxyalkylene group.

3. The mixture of amines of claim 2, where the alkoxyalkylene group has the structure $R^8$—O—$R^9$—, where $R^8$ is independently an alkyl radical of 1 to 5 carbon atoms and $R^9$ is independently an alkylene radical of 1 to 5 carbon atoms.

4. The mixture of amines of claim 2 further comprising the presence of a dialdehyde selected from the group consisting of glyoxal, glutaraldehyde, succinic aldehyde, adipic aldehyde and mixtures thereof, where the dialdehyde is blended or reacted with the mixture of amines.

5. The mixture of amines of claim 2 further comprising the presence of glyoxal, where the glyoxal is blended or reacted with the mixture of amines.

6. A mixture of amines made by reacting at least one amine compound selected from the group consisting of $R^1NH_2$; $R^3NH_2$; $R_5NH_2$ and $R^7_2NH$ with at least one aldehyde compound selected from the group consisting of $R^2CHO$, $R^4CHO$ and $R^6CHO$;

where $R^1$, $R^3$ and $R^5$ are independently selected from the group consisting of hydrogen and an alkyl radical, including substituted alkyl radicals, of 1 to 5 carbon atoms; and $R^7$ is independently $R^1$, $R^3$ or $R^5$;

where $R^2$, $R^4$ and $R^6$ are independently selected from the group consisting of hydrogen and an alkyl radical, including substituted alkyl radicals, of 1 to 5 carbon atoms; and where at least one of the $R^1$, $R^2$, $R^{3,}$ $R^4$, $R^5$, and $R^6$ groups is an alkoxyalkylene group.

7. The mixture of amines of claim 6 where the molar ratio of amines to aldehydes ranges from 10:1 to 1:10.

8. The mixture of amines of claim 6 further comprising a dialdehyde selected from the group consisting of glyoxal, glutaraldehyde, succinic aldehyde, adipic aldehyde and mixtures thereof, blended therewith.

9. The mixture of amines of claim 6 further comprising reacting the amine compound with the aldehyde compound in the presence of a dialdehyde as a coreactant therewith, the dialdehyde being selected from the group consisting of glyoxal, glutaraldehyde, succinic aldehyde, adipic aldehyde and mixtures thereof.

10. The mixture of amines of claim 6 where the mixture of amines is made by combining a formulation comprising formaldehyde; an amine selected from the group consisting of methoxypropylamine, ethoxypropylamine and mixtures thereof and glyoxal, prior to reacting.

11. The mixture of amines of claim 6 where the mixture of amines is made by combining a formulation comprising:

| | |
|---|---|
| methylamine | 0–40 wt. % |
| formaldehyde | 15–30 wt. % |
| methoxypropylamine | 10–30 wt. % |
| glyoxal | 0–15 wt. % | prior to reacting.

12. The mixture of amines of claim 6 made by the process comprising the steps of:

reacting a first amine compound with a first aldehyde compound to form a first reaction product amine mixture;

reacting a second amine compound with a second aldehyde compound to form a second reaction product amine mixture, where the second amine compound is not the same as the first amine compound, and where the second aldehyde compound may be the same as or different from the second amine compound;

mixing the first reaction product amine mixture with the second reaction product amine mixture to form an intermediate mixture; and adding a dialdehyde to the intermediate mixture to form the final product mixture of amines.

13. The mixture of amines of claim 12 where the first amine compound is methylamine, the second amine compound is methoxypropylamine, the first and second aldehyde compounds are both formaldehyde and the dialdehyde is glyoxal.

14. A mixture of amines useful in reducing levels of hydrogen sulfide ($H_2S$) in a gaseous or liquid stream containing $H_2S$, the mixture comprising a reaction product of a hexahydrotriazine of the formula:

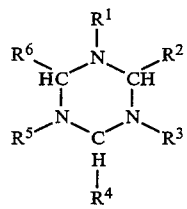

(i)

where $R^1$, $R^3$ and $R^5$ are independently selected from the group consisting of hydrogen and an alkyl radical, including substituted alkyl radicals, of 1 to 5 carbon atoms; and where $R^2$, $R^4$ and $R^6$ are independently selected from the group consisting of hydrogen and an alkyl radical, including substituted alkyl radicals, of 1 to 5 carbon atoms; and a dialdehyde.

15. A mixture of amine components comprising at least two of the following amines:

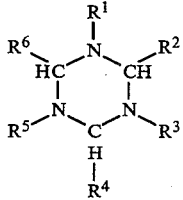

(i)

where $R^1$, $R^3$ and $R^5$ are independently selected from the group consisting of hydrogen and an alkyl radical, including substituted alkyl radicals, of 1 to 5 carbon atoms;

where $R^2$, $R^4$ and $R^5$ are independently selected from the group consisting of hydrogen and an alkyl radical, including substituted alkyl radicals, of 1 to 5 carbon atoms; and

(ii) $RN=CHR$;

(iii) $R^2NCH(R')NR^2$; and (iv) $R^2NCH(R')OH$;

where R may independently be $R^1$, $R^2$, $R^3$, $R^4$, $R^5$ and $R^5$, and where R' may independently be alkylene radicals equivalent to $R^1$, $R^2$, $R^3$, $R^4$, $R^5$ and $R^{6;}$ and including at least one dialdehyde.

16. A mixture of amines made by reacting at least one amine compound selected from the group consisting of $R^1NH_2$; $R^3NH_2$; $R^5NH_2$ and $R^7{}_2NH$ with at least one aldehyde compound selected from the group consisting of $R^2CHO$, $R^4CHO$ and $R^6CHO$, in the presence of at least one dialdehyde;

where $R^1$, $R^3$ and $R^5$ are independently selected from the group consisting of hydrogen and an alkyl radical, including substituted alkyl radicals, of 1 to 5 carbon atoms; and $R^7$ is independently $R^1$, $R^3$ or $R^5$;

where $R^2$, $R^4$ and $R^6$ are independently selected from the group consisting of hydrogen and an alkyl radical, including substituted alkyl radicals, of 1 to 5 carbon atoms.

17. A process for making a mixture of amines comprising reacting at least one amine compound selected from the group consisting of $R^1NH_2$; $R^3NH_2$; $R^5NH_2$ and $R^7{}_2NH$ with at least one aldehyde compound selected from the group consisting of $R^2CHO$, $R^4CHO$ and $R^6CHO$;

where $R^1$, $R^3$ and $R^5$ are independently selected from the group consisting of hydrogen and an alkyl radical, including substituted alkyl radicals, of 1 to 5 carbon atoms; where at least one of the groups is an alkoxyalkylene group; and $R^7$ is independently $R^1$, $R^3$ or $R^5$;

where $R^2$, $R^4$ and $R^6$ are independently selected from the group consisting of hydrogen and an alkyl radical, including substituted alkyl radicals, of 1 to 5 carbon atoms; and where at least one of the $R^1$, $R^2$, $R^3$, $R^4$, $R^5$, and $R^6$ groups is an alkoxyalkylene group.

18. The process of claim 17 where the molar ratio of amines to aldehydes ranges from 10:1 to 1:10.

19. The process of claim 17 where a dialdehyde is present during the reacting, the dialdehyde being selected from the group consisting of glyoxal, glutaraldehyde, succinic aldehyde, adipic aldehyde and mixtures thereof, where the dialdehyde is blended or reacted with the mixture of amines.

20. The process of claim 17 where the amine compound and aldehyde compound are reacted at a temperature in the range of about 0 to about 150 ° C., and at a pressure in the range of about atmospheric to about 200 psig.

21. The process of claim 17 where the mixture of amines is made by combining a formulation comprising formaldehyde; an amine selected from the group consisting of methoxypropylamine, ethoxypropylamine and mixtures thereof and glyoxal prior to reacting.

22. The process of claim 17 where the mixture of amines is made by combining a formulation comprising:

| | |
|---|---|
| methylamine | 0–40 wt. % |
| formaldehyde | 15–30 wt. % |
| methoxypropylamine | 10–30 wt. % |
| glyoxal | 0–15 wt. % | prior to reacting.

23. The process of claim 17 further comprising the steps of:

reacting a first amine compound with a first aldehyde compound to form a first reaction product amine mixture;

reacting a second amine compound with a second aldehyde compound to form a second reaction product amine mixture, where the second amine compound is not the same as the first amine compound, and where the second aldehyde compound may be the same as or different from the second amine compound;

mixing the first reaction product amine mixture with the second reaction product amine mixture to form an intermediate mixture; and adding a dialdehyde to the intermediate mixture to form the final product mixture of amines.

24. The process of claim 17 where the mole ratio of amines to aldehydes is about 1:1.

* * * * *

UNITED STATES PATENT AND TRADEMARK OFFICE
CERTIFICATE OF CORRECTION

PATENT NO. : 5,347,004
DATED : September 13, 1994
INVENTOR(S) : Gordon T. Rivers, et al.

It is certified that error appears in the above-indentified patent and that said Letters Patent is hereby corrected as shown below:

At column 2, line 45, please delete "groups" and insert --groups $R^1$, $R^2$, $R^3$, $R^4$, $R^5$, and $R^6$,-- therefor.

At column 3, line 63, please delete "preferred" and insert --preferred.-- therefor.

At column 4, line 6, please delete "$R^8$-O-$R^9$" and insert --$R^8$-O-$R^9$- -- therefor.

At column 5, line 51, please delete "psigh" and insert --psig-- therefor.

At column 7, line 32, please delete

"$CH_3OCH_2CH_2CH_2NHCH_2NHCH_2CH_2CH_2OCH_{3+CH3}NHCH_2NHCH_3+CH_3OCH_2CH_2NHCH_2NHCH_3$," and insert --$CH_3OCH_2CH_2CH_2NHCH_2NHCH_2CH_2CH_2OCH_3$ +$CH_3NHCH_2NHCH_3$+$CH_3OCH_2CH_2NHCH_2NHCH_3$-- therefor.

At column 7, line 45, please delete "SCFFI" and insert --SCFH-- therefor.

At column 10, line 46, please delete "RS" and insert --$R^5$-- therefor.

At column 10, line 68, please delete "$R_5NH_2$" and insert --$R^5NH_2$-- therefor.

At column 11, line 7, please delete "RS" and insert --$R^5$-- therefor.

At column 12, line 23, please insert -- (i) a hexahydrotriazine of the formula:-- therefor.

UNITED STATES PATENT AND TRADEMARK OFFICE
CERTIFICATE OF CORRECTION

PATENT NO. : 5,347,004
DATED : September 13, 1994
INVENTOR(S) : Gordon T. Rivers, et al.

It is certified that error appears in the above-indentified patent and that said Letters Patent is hereby corrected as shown below:

At column 12, line 38, please delete "$R^5$" and insert --$R^6$-- therefor.

At column 12, line 43, please delete "$R^2NCH(R')NR^2$" and insert --$R^2NCH(R')NR_2$-- therefor.

At column 12, line 44, please delete "$R^2NCH(R')OH$" and insert --$R_2NCH(R')OH$-- therefor.

At column 12, line 46, please delete "$R^5$" and insert --$R^6$-- therefor.

Signed and Sealed this

Twenty-first Day of May, 1996

Attest:

BRUCE LEHMAN

*Attesting Officer*     *Commissioner of Patents and Trademarks*